United States Patent
Pacetti

(10) Patent No.: US 9,603,976 B2
(45) Date of Patent: Mar. 28, 2017

(54) BIODEGRADABLE COATINGS FOR IMPLANTABLE MEDICAL DEVICES

(71) Applicant: Abbott Cardiovascular Systems Inc., Santa Clara, CA (US)

(72) Inventor: Stephen Dirk Pacetti, San Jose, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 151 days.

(21) Appl. No.: 14/323,816

(22) Filed: Jul. 3, 2014

(65) Prior Publication Data

US 2014/0322294 A1  Oct. 30, 2014

Related U.S. Application Data

(60) Division of application No. 12/023,953, filed on Jan. 31, 2008, now Pat. No. 8,791,171, which is a continuation-in-part of application No. 10/428,691, filed on May 1, 2003, now Pat. No. 7,563,454.

(51) Int. Cl.
| | | |
|---|---|---|
| *A61F 2/00* | (2006.01) |
| *A61L 31/10* | (2006.01) |
| *A61L 27/34* | (2006.01) |
| *A61L 31/14* | (2006.01) |
| *A61L 27/00* | (2006.01) |
| *A61L 31/08* | (2006.01) |
| *A61L 27/14* | (2006.01) |

(52) U.S. Cl.
CPC .............. *A61L 31/10* (2013.01); *A61L 27/34* (2013.01); *A61L 31/148* (2013.01); *A61L 27/00* (2013.01); *A61L 27/14* (2013.01); *A61L 31/08* (2013.01); *A61L 2420/00* (2013.01); *A61L 2420/02* (2013.01)

(58) Field of Classification Search
None
See application file for complete search history.

(56) References Cited

U.S. PATENT DOCUMENTS

2005/0201974 A1* 9/2005 Schestopol .......... A61K 9/0065
424/78.27
2009/0093610 A1* 4/2009 Textor .............. A61K 47/48215
528/363

\* cited by examiner

*Primary Examiner* — James Rogers
(74) *Attorney, Agent, or Firm* — Squire Patton Boggs (US) LLP

(57) ABSTRACT

Biodegradable coatings for implantable medical devices are disclosed.

4 Claims, No Drawings

BIODEGRADABLE COATINGS FOR IMPLANTABLE MEDICAL DEVICES

RELATED APPLICATIONS

This application is a divisional application of U.S. patent application Ser. No. 12/023,953 filed on Jan. 31, 2008, which is a continuation-in-part of U.S. patent application Ser. No. 10/428,691 filed on May 1, 2003, the teachings of which are incorporated by reference in their entirety.

FIELD OF THE INVENTION

The present invention is directed to biodegradable coatings for implantable medical devices.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorption and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused portion's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents may be accomplished using implantable medical devices. Coating implantable medical devices with therapeutic agents, however, is not without problems.

The family of mussel adhesive proteins is unique in that they bond to a large variety of substrates in an aqueous environment. These proteins share numerous molecular motifs, however, approximately 25% of amino acids in a particular mussel adhesive protein is the modified amino acid 3,4-dihydroxyphenyl-L-alanine (DOPA). It has further been determined that mussel adhesion to rocks, wood and metal is due in large part to DOPA. It has been found, however, that the portion of DOPA responsible for the remarkable adhesive capability of these polymers is the 3,4-dihydroxyphenyl group. The present invention takes advantage of the strong binding properties of 3,4-dihydroxyphenyl, and 2,3-dihydroxyphenyl, to provide novel biodegradable coatings, primarily for use as primer coatings for implantable medical devices, particularly bare metal implantable medical devices.

SUMMARY

The present invention relates to a biodegradable coating for an implantable medical device that includes a biodegradable polymer functionalized with an ortho-dihydroxyphenyl compound, the overall structure having the formula:

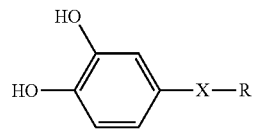

where X is a linker group and R is the biodegradable polymer.

In various aspects, R includes a polyester which can be selected from a group that includes a poly(glycolide), poly(D,L-lactide), poly(L-lactide), poly(D,L-lactide-co-glycolide), poly(caprolactone), poly(dioxanone), poly(glycolide-co-trimethylenecarbonate) and copolymers thereof.

In various aspects, R includes a poly(esteramide), poly(tyrosine-derived carbonate), a poly(tyrosine-derived ester), a poly(tyrosine-α-hydroxyacid), a poly(orthoester) or a biodegradable polyurethane.

In various aspects, R includes a poly(depsipeptide) which in some aspects can have the general formula:

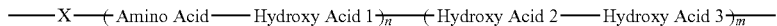

where X is the linker group. In this aspect, the amino acid can be selected from the group consisting of aspartic acid, glutamic acid, lysine, cysteine, serine, threonine and tyrosine. In this aspect, hydroxy acid 1, hydroxy acid 2 and hydroxy acid 3 can be independently selected from a group that includes glycolic acid, L-lactic acid, D-lactic acid, D,L-lactic acid, meso-lactic acid, caprolactone, dioxanone, β-butyrolactone, β-propiolactone and β-valerolactone.

In various aspects, the linker group can include between 1 and 16 carbon atoms.

In various aspects, the linker group is linear, branched, unsaturated or cycloaliphatic. In various aspects, the linker group comprises an ester, an amide, an ether, an anhydride, a sulfoester, a thioether, a sulfone, a phosphonate, a phosphoester, a carbonate, an imino-carbonate, an acetal, a ketal, an imine, an ortho-ester, a sulfamide or a urethane bond.

In various aspects, the biodegradable polymer can be functionalized with two ortho-dihydroxyphenyl compounds, the overall structure having the formula:

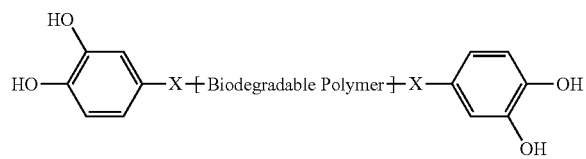

where X independently comprises a linear, branched, unsaturated or cycloaliphatic linker.

In various aspects, the biodegradable polymer can be functionalized with multiple ortho-dihydroxyphenyl compounds, the overall structure having the formula:

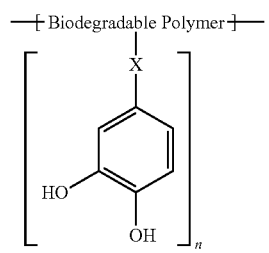

where X independently comprises a linear, branched, unsaturated or cycloaliphatic linker.

Another aspect of the invention relates to an implantable medical device that includes a coating according to the invention. The implantable medical device can be a stent.

DETAILED DESCRIPTION

The present invention provides a biodegradable coating for an implantable medical device that includes a biodegradable polymer functionalized with an ortho-dihydroxyphenyl compound, the overall structure having formula I:

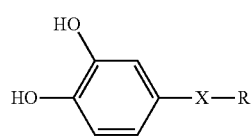

where X is a linker group and R is the biodegradable polymer.

In various aspects, a biodegradable polymer can be functionalized with a different ortho-dihydroxyphenyl compound, the overall structure having formula II:

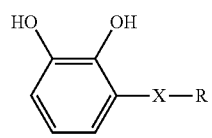

where X is a linker group and R is the biodegradable polymer.

It is to be understood that both of the ortho-dihydroxyphenyl compounds depicted by formulas I and II above are suitable for coatings of the present invention although compounds with the structure according to formula I are presently preferred.

As used herein, "biodegradable" refers to materials that are capable of being degraded or absorbed when exposed to bodily fluids such as blood, and components thereof such as enzymes or oxidative species, and that can be gradually absorbed and/or eliminated by the body.

In various aspects, R includes a polyester which can be selected from a group that includes a poly(glycolide), poly (D,L-lactide), poly(L-lactide), poly(D,L-lactide-co-glycolide), poly(caprolactone), poly(dioxanone), poly(glycolide-co-trimethylenecarbonate) and copolymers thereof.

When the biodegradable coating is used as a primer layer on an implantable medical device and a drug reservoir layer is disposed over the primer layer, the R group can be chosen to be compatible with the reservoir layer polymer. For example, if a drug reservoir layer includes poly(D,L-lactide), then a primer layer would be chosen, without limitation, to also include poly(D,L-lactide), an example of which is shown by formula III.

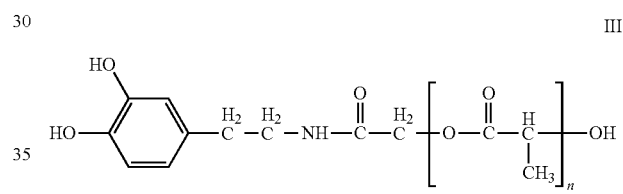

The synthesis of this polymer involves ring-opening polymerization using D,L-lactide and glycolic acid as the initiator. This yields an acid functional poly(D,L-lactide). Dopamine is then coupled to the carboxyl endgroup, methods of which are known to those skilled in the art.

The polymer of formula III can attach to a metal surface, e.g., a bare metal stent, by ortho-dihydroxyphenyl endpoint attachment. If the polyester polymer segment is too large however, it is unlikely that the ortho-dihydroxyphenyl would effectively coordinate with the metal surface. Thus, the polymer will be chosen to be less than 20,000 Daltons.

In an alternative embodiment, an ortho-dihydrophenyl moiety can be present at both termini of a biodegradable polymer, as shown by formula IV:

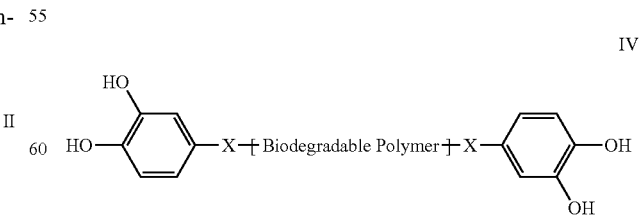

Synthesis of this moiety can be accomplished using methods known to those skilled in the art, such as that depicted below:

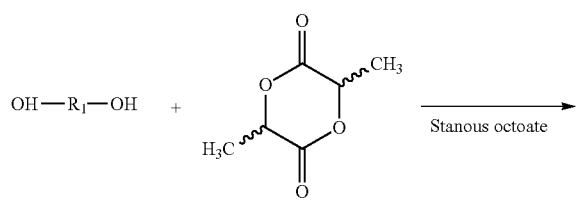
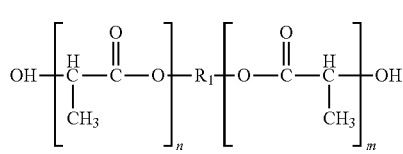

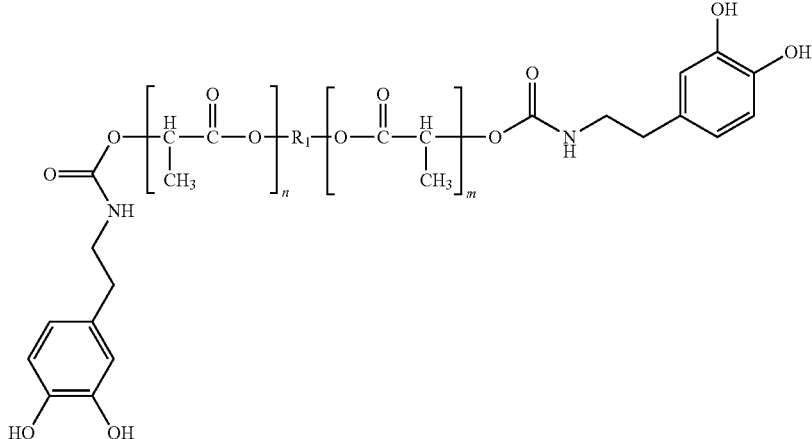

In this pathway, $R_1$ may be a $C_2$ to $C_{16}$ linear, branched, unsaturated or cyclic hydrocarbon. When this structure is used as a primer coating for a metal implantable device, the two ortho-dihydroxyphenyl moieties will attach to the device surface, thereby forming a loop-like structure on the device.

Biodegradable primers containing a much higher number of ortho-dihydroxy phenyl groups are also encompassed by the present invention. For example, the biodegradable polymer can be functionalized with multiple ortho-dihydroxyphenyl compounds having an overall structure with the formula:

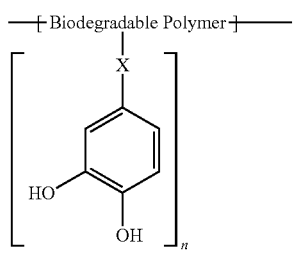

where X independently comprises a linear, branched, unsaturated or cycloaliphatic linker. In this aspect, the ortho-dihydroxyphenyl moieties can be attached to the biodegradable polymer as grafts or as pendant groups.

Similarly, a poly(depsipeptide) wherein the amino acid is aspartic acid, glutamic acid or lysine are possible according to the invention. As used herein, "poly(depsipeptide)" refers to a polypeptide in which one or more of the amide bonds are replaced by ester bonds. An exemplary poly(depsipeptide) is depicted by formula V below:

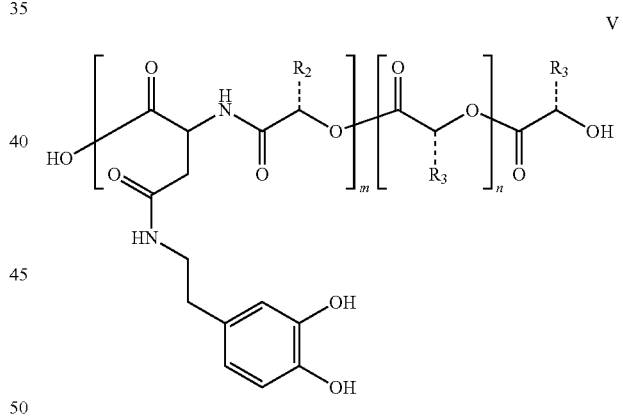

In this aspect of the invention, $R_2$ and $R_3$ can independently be either hydrogen or a methyl group. This structure allows for any number of ortho-dihydroxyphenyl groups up to that matching the monomer number "m". In this family of poly(depsipeptides), two cyclic monomers are used to produce the polymer. One monomer bears the protected amino acid side chain that is used to conjugate the dopamine or other ortho-dihydroxyphenyl group. The second cyclic monomer is a conventional ring opening monomer such as glycolide, lactide, dioxanone, β-butyrolactone, β-propiolactone or caprolactone. A schematic showing presently preferred amino acids and hydroxyl acids in the first block and the possible ring opening monomers in the second block is depicted below:

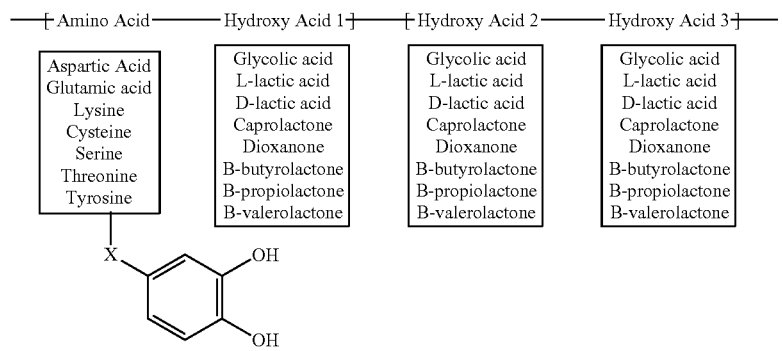

In this aspect, hydroxy acid 1, hydroxy acid 2 and hydroxy acid 3 can be independently selected from a group that includes glycolic acid, L-lactic acid, D-lactic acid, caprolactone, dioxanone, β-butyrolactone, β-propiolactone and β-valerolactone. These amino acids include those with R-groups that could be used for attachment of an ortho-dihydroxyphenyl group. Aspartic acid, glutamic acid and lysine are presently preferred.

An ortho-dihydroxyphenyl group of the invention can also be added to other biodegradable polymers including poly(esteramides), poly(tyrosine-derived carbonates), poly(tyrosine-derived esters), poly(tyrosine-alphahydroxyacids) and biodegradable polyurethanes.

An example of a poly(tyrosine-derived carbonate) wherein the ortho-dihydroxyphenyl group is present as a conjugated dopamine and the amount of ortho-dihydroxyphenyl can be adjusted by varying the ratio of "m" to "n" is depicted by formula VI.

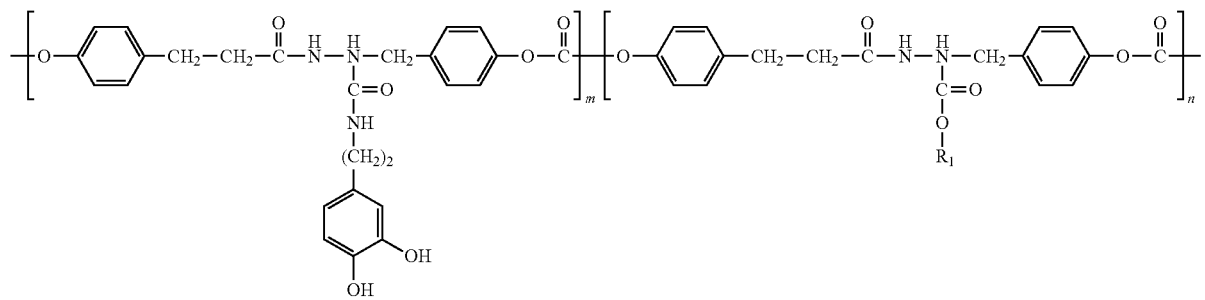

VI $R_1$ can be any $C_1$ to $C_{16}$ linear, branched, cycloaliphatic, aromatic or unsaturated hydrocarbon. Methods of synthesizing the precursor to the compound of formula VI are known in the art.

An example of a poly(tyrosine-derived ester) is depicted by formula VII.

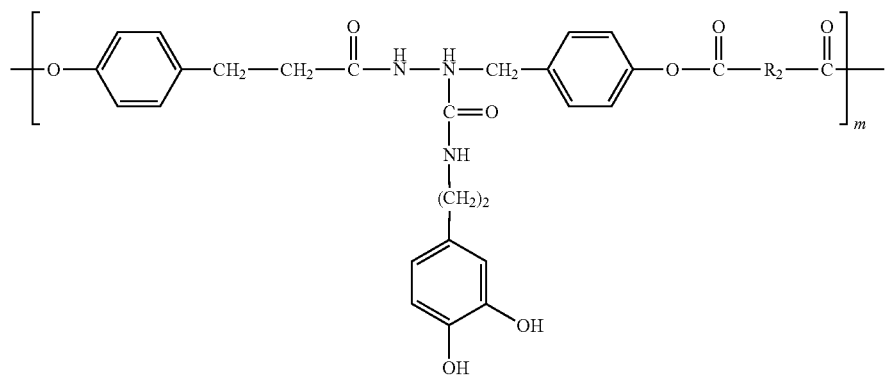

VII

-continued

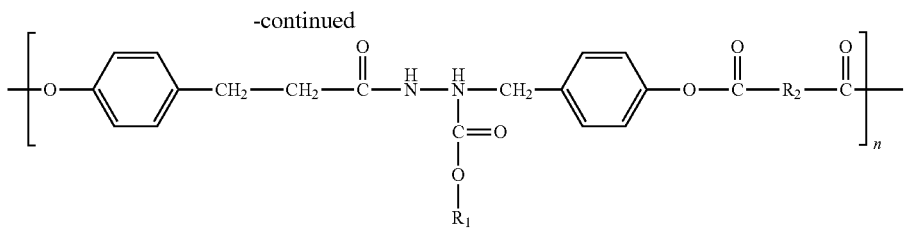

As in formula VI above, the amount of ortho-dihydroxyphenyl substitution can be controlled by the amount of the first monomer. $R_1$ may be any $C_1$ to $C_{16}$ linear, branched, cycloaliphatic, aromatic, unsaturated hydrocarbon, poly(ethylene glycol), polypropylene glycol), or poly(tetramethylene glycol). Methods of synthesizing this type of poly(tyrosine-derived ester) are known to those skilled in the art.

It is to be understood that while the biodegradable coatings of the invention are primarily intended to be used as primer layers on an implantable medical device, they also may serve as drug reservoir layers.

Another aspect of the invention relates to an implantable medical device comprising a coating according to the invention.

As used herein, "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators, leads and electrodes for the preceding, implantable organ stimulators such as nerve, bladder, sphincter and diaphragm stimulators, cochlear implants, prostheses, vascular grafts, self-expandable stents, balloon-expandable stents, stent-grafts, AV fistulas, grafts, PFO closure devices, arterial closure devices, artificial heart valves and cerebrospinal fluid shunts.

At present, preferred implantable medical devices for use with coatings of this invention are stents.

A stent refers generally to any device used to hold tissue in place in a patient's body. Particularly useful stents are those used for the maintenance of the patency of a vessel in a patient's body when the vessel is narrowed or closed due to diseases or disorders including, without limitation, tumors (in, for example, bile ducts, the esophagus or the trachea/bronchi), benign pancreatic disease, coronary artery disease, carotid artery disease, renal artery disease and peripheral arterial disease such as atherosclerosis, restenosis and vulnerable plaque. For example, a stent can be used to strengthen the wall of the vessel in the vicinity of a vulnerable plaque (VP). VP refers to a fatty build-up in an artery thought to be caused by inflammation. The VP is covered by a thin fibrous cap that can rupture leading to blood clot formation. Thus, a stent can not only maintain vessel patency but can act as a shield against VP rupture. A stent can be used in, without limitation, neuro, carotid, coronary, pulmonary, aortic, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. Indeed, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. A stent coating must be flexible and capable of elongation.

Examples of stent materials include stainless steel, nitinol, tantalum, tantalum alloy, titanium, titanium alloy, cobalt chromium alloys, cobalt nickel alloys, platinum modified stainless steel, nickel-titanium-platinum alloys, niobium, niobium alloy, zirconium and zirconium alloy.

It is to be understood that an implantable medical device of the invention will have coated on it's surface at least one layer of a biologically compatible coating of the invention, although any number of coating layers are encompassed by the invention.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A biodegradable coating comprising a biodegradable polymer having the following formula:

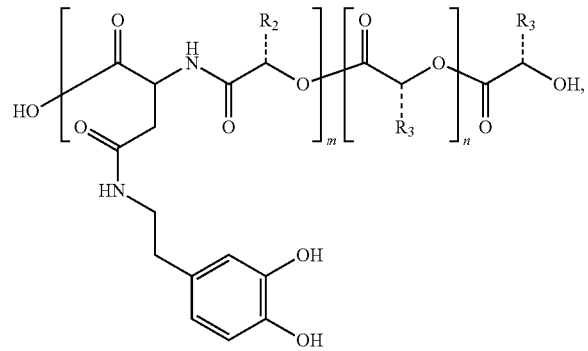

wherein $R_2$ and $R_3$ are independently hydrogen or methyl group, m and n each are a positive integer.

2. An implantable medical device comprising the coating according to claim 1.

3. The implantable medical device of claim 2, wherein the implantable medical device comprises a stent.

4. An implantable medical device comprising a drug reservoir layer and a primer layer, wherein the primer layer is the coating according to claim 1, and the drug reservoir layer is disposed over the primer layer.

* * * * *